(12) United States Patent
Sakai et al.

(10) Patent No.: US 10,786,143 B2
(45) Date of Patent: Sep. 29, 2020

(54) OPTICAL MODULE, IMAGE PICKUP MODULE, AND ENDOSCOPE

(71) Applicant: OLYMPUS CORPORATION, Tokyo (JP)

(72) Inventors: Youhei Sakai, Ina (JP); Hideharu Miyahara, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/413,665

(22) Filed: May 16, 2019

(65) Prior Publication Data
US 2019/0261839 A1    Aug. 29, 2019

Related U.S. Application Data

(63) Continuation of application No. PCT/JP2016/084070, filed on Nov. 17, 2016.

(51) Int. Cl.
*A61B 1/04*     (2006.01)
*G02B 6/42*     (2006.01)
(Continued)

(52) U.S. Cl.
CPC ............ *A61B 1/04* (2013.01); *A61B 1/00013* (2013.01); *G02B 6/42* (2013.01); *H01L 25/065* (2013.01); *H01L 25/07* (2013.01); *H01L 25/18* (2013.01); *H01L 27/14* (2013.01); *H04N 5/225* (2013.01); *H04N 5/369* (2013.01); *H04N 7/18* (2013.01)

(58) Field of Classification Search
CPC ....... A61B 1/04; A61B 1/00013; A61B 1/051; G02B 6/42; G02B 6/423; G02B 6/4239; H01L 25/065; H01L 25/07; H01L 25/18; H01L 27/14; H04N 5/225; H04N 5/369; H04N 5/2256; H04N 5/2253; H04N 7/18
See application file for complete search history.

(56) References Cited

U.S. PATENT DOCUMENTS

| 5,220,198 | A | 6/1993 | Tsuji | |
|---|---|---|---|---|
| 2015/0318924 | A1* | 11/2015 | Motohara | ............ G02B 6/4259 398/200 |

FOREIGN PATENT DOCUMENTS

| EP | 2 947 486 A1 | 11/2015 |
|---|---|---|
| JP | H04-218136 A | 8/1992 |

(Continued)

OTHER PUBLICATIONS

International Search Report dated Feb. 28, 2017 issued in International Application No. PCT/JP2016/084070.

*Primary Examiner* — Ryan A Lepisto
(74) *Attorney, Agent, or Firm* — Scully, Scott, Murphy & Presser, P.C.

(57) ABSTRACT

An optical module includes an optical element including a light emitting section, a first wiring board, on a first principal plane of which the optical element is mounted, a ferrule functioning as a holding member including a through hole and disposed on a second principal plane of the first wiring board, an optical fiber inserted into the through hole of the ferrule, a side surface wiring board, a third principal plane of which is disposed in parallel to an optical axis and an end portion of which is connected to the first wiring board, an electrode being disposed on a fourth principal plane of the side surface wiring board, and a signal cable having a distal end portion bonded to the electrode of the side surface wiring board.

8 Claims, 15 Drawing Sheets

(51) Int. Cl.
*H01L 25/065* (2006.01)
*H01L 25/07* (2006.01)
*H01L 25/18* (2006.01)
*H01L 27/14* (2006.01)
*H04N 5/225* (2006.01)
*H04N 5/369* (2011.01)
*A61B 1/00* (2006.01)
*H04N 7/18* (2006.01)

(56) References Cited

FOREIGN PATENT DOCUMENTS

| | | |
|---|---|---|
| JP | H05-049602 A | 3/1993 |
| JP | 2008-118568 A | 5/2008 |
| JP | 2014-137584 A | 7/2014 |
| JP | 2015-068835 A | 4/2015 |
| WO | 2005/057262 A1 | 6/2005 |
| WO | 2014/112461 A1 | 7/2014 |

\* cited by examiner

OPTICAL MODULE, IMAGE PICKUP MODULE, AND ENDOSCOPE

CROSS REFERENCE TO RELATED APPLICATION

This application is a continuation application of PCT/JP2016/084070 filed on Nov. 17, 2016, the entire contents of which are incorporated herein by this reference.

BACKGROUND OF THE INVENTION

1. Field of the Invention

The present invention relates to an optical module including an optical element configured to transmit or receive an optical signal, an optical fiber for transmitting the optical signal, a holding member configured to hold the optical fiber, and a signal cable for transmitting an electric signal, an image pickup module including the optical module and an image pickup device, and an endoscope including the image pickup module.

2. Description of the Related Art

An endoscope includes an image pickup module including an image pickup device such as a CCD at a distal end portion of an elongated insertion section. In recent years, use of an image pickup device including a large number of pixels in the endoscope has been examined. When an image pickup device including a large number of pixels is used, a signal amount transmitted from the image pickup device to a signal processing apparatus increases. Therefore, optical signal transmission via an optical fiber by an optical signal is desirable instead of electric signal transmission via a metal wire by an electric signal. For the optical signal transmission, an E/O optical transmission module (an electrooptic converter) that converts an electric signal into an optical signal and an O/E optical transmission module (a photoelectric converter) that converts an optical signal into an electric signal are used.

In an optical module and an image pickup module, in particular, an optical module and an image pickup module disposed at a distal end portion of an endoscope, a reduction in a diameter and a reduction in length are important problems.

For example, Japanese Patent Application Laid-Open Publication No. 2014-137584 discloses an image pickup module that converts an electric signal outputted by an image pickup device into an optical signal with a surface emitting laser (VCSEL), which is an optical element, and transmits the optical signal via an optical fiber held by a ferrule. A signal cable for transmitting an electric signal to the image pickup device and the optical element is connected to a wiring board on which the image pickup device, the optical element, and the ferrule are disposed.

SUMMARY OF THE INVENTION

An optical module according to an embodiment of the present invention includes: an optical element including a light emitting section or a light receiving section; a first wiring board including a first principal plane and a second principal plane opposite to the first principal plane, the optical element being mounted on the first principal plane; a holding member disposed on the second principal plane of the first wiring board such that a center axis of a through hole coincides with an optical axis of the optical element; an optical fiber inserted into the through hole of the holding member; a side surface wiring board including a third principal plane and a fourth principal plane opposite to the third principal plane, the third principal plane being disposed in parallel to the optical axis, an end portion of the side surface wiring board being connected to the first wiring board, an electrode being disposed on at least one of the third principal plane and the fourth principal plane; and a signal cable having a distal end portion bonded to the electrode of the side surface wiring board. The side surface wiring board extends to a second principal plane side of the first wiring board.

An image pickup module according to another embodiment of the present invention includes: an optical element including a light emitting section or a light receiving section; a first wiring board including a first principal plane and a second principal plane opposite to the first principal plane, the optical element being mounted on the first principal plane; a holding member disposed on the second principal plane of the first wiring board such that a center axis of a through hole coincides with an optical axis of the optical element; an optical fiber inserted into the through hole of the holding member; a side surface wiring board including a third principal plane and a fourth principal plane opposite to the third principal plane, the third principal plane being disposed in parallel to the optical axis, an end portion of the side surface wiring board being connected to the first wiring board, an electrode being disposed on at least one of the third principal plane and the fourth principal plane; a signal cable having a distal end portion bonded to the electrode of the side surface wiring board; an image pickup device including a light receiving surface and a rear surface opposite to the light receiving surface and configured to output an image pickup signal; a second wiring board including a fifth principal plane and a sixth principal plane opposite to the fifth principal plane, the image pickup device being bonded to the fifth principal plane; and an interconnecting wiring board connecting the first wiring board and the second wiring board. The side surface wiring board extends to a second principal plane side of the first wiring board.

An endoscope according to still another embodiment of the present invention includes an image pickup module. The image pickup module includes: an optical element including a light emitting section or a light receiving section; a first wiring board including a first principal plane and a second principal plane opposite to the first principal plane, the optical element being mounted on the first principal plane; a holding member disposed on the second principal plane of the first wiring board such that a center axis of a through hole coincides with an optical axis of the optical element; an optical fiber inserted into the through hole of the holding member; a side surface wiring board including a third principal plane and a fourth principal plane opposite to the third principal plane, the third principal plane being disposed in parallel to the optical axis, an end portion of the side surface wiring board being connected to the first wiring board, an electrode being disposed on at least one of the third principal plane and the fourth principal plane; a signal cable having a distal end portion bonded to the electrode of the side surface wiring board; an image pickup device including a light receiving surface and a rear surface opposite to the light receiving surface and configured to output an image pickup signal; a second wiring board including a fifth principal plane and a sixth principal plane opposite to the fifth principal plane, the image pickup device being bonded to the fifth principal plane; and an interconnecting wiring board connecting the first wiring board and the second wiring board. The side surface wiring board extends to a second principal plane side of the first wiring board.

DETAILED DESCRIPTION OF THE PREFERRED EMBODIMENTS

<First Embodiment>

Figure 1:
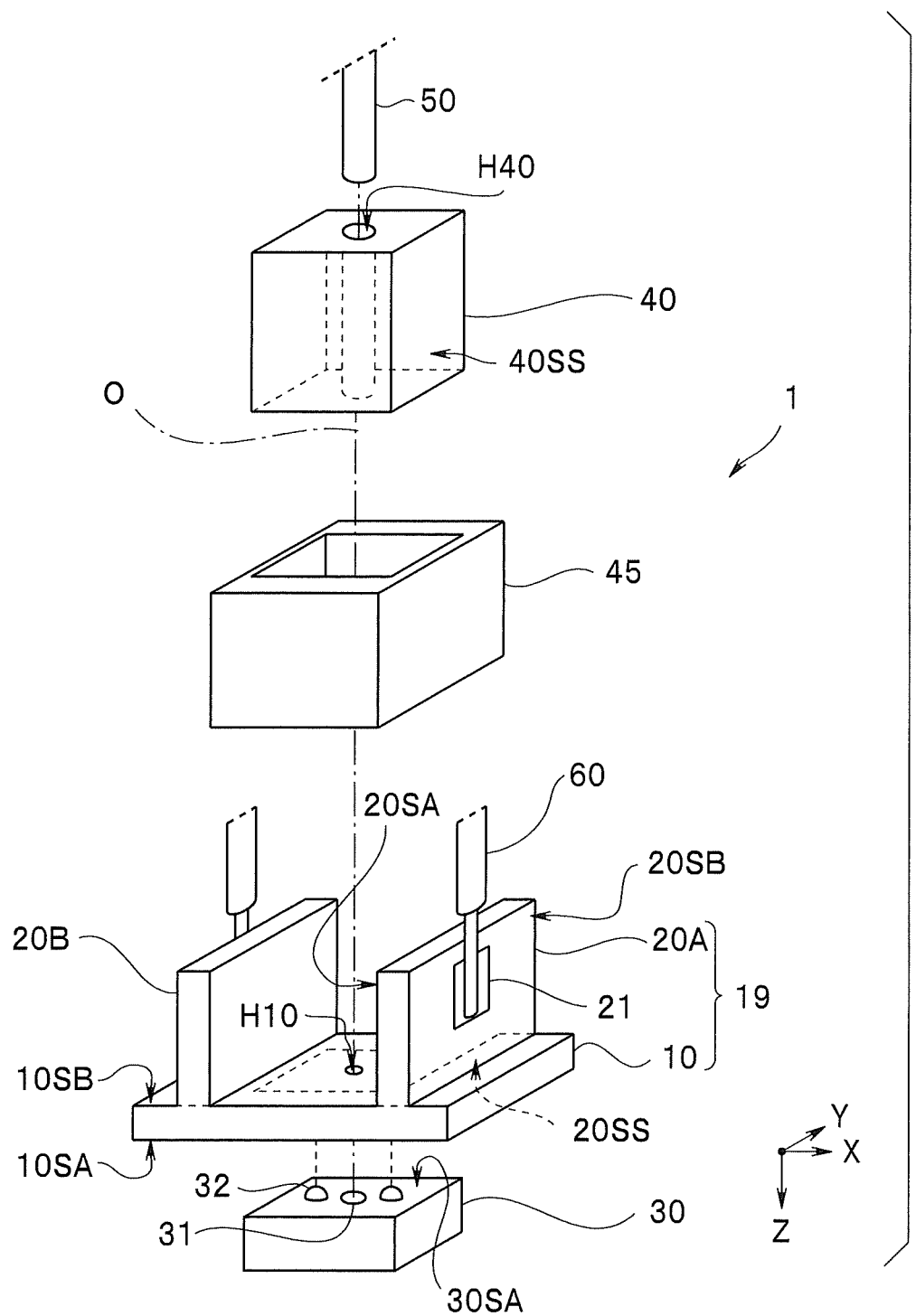
FIG. 1 is an exploded view of an optical module in a first embodiment.
Figure 2:
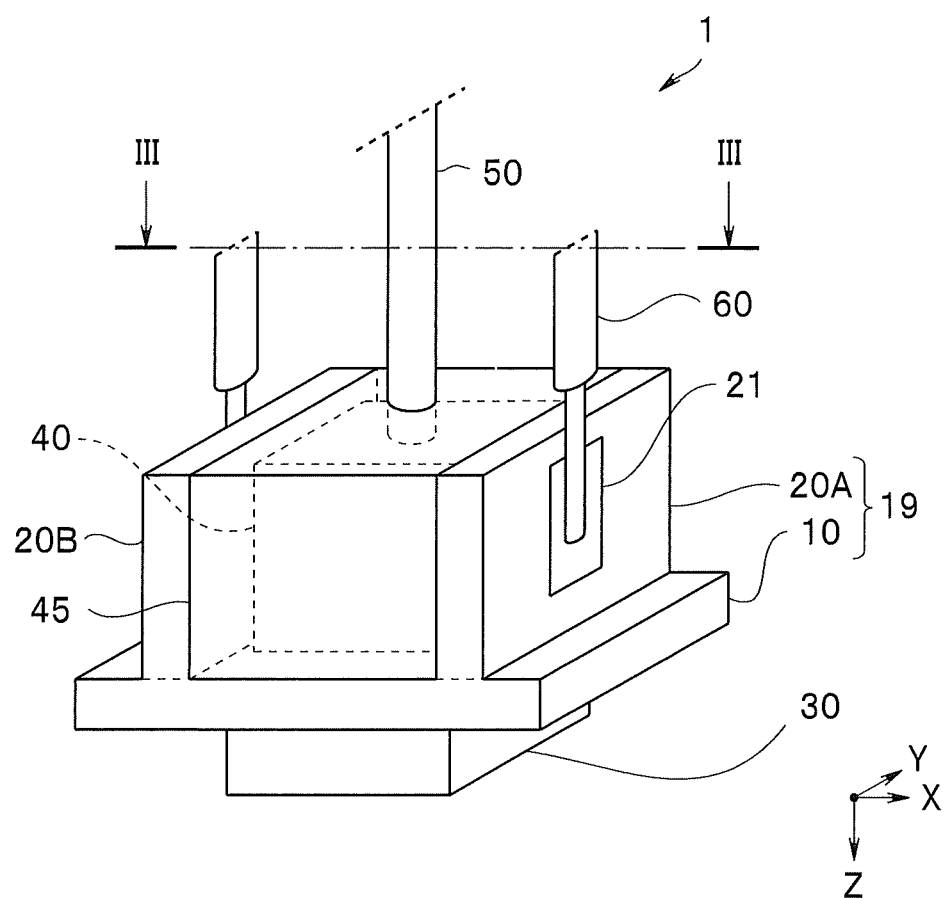
FIG. 2 is a perspective view of the optical module in the first embodiment.

An optical module 1 in this embodiment is explained with reference to FIG. 1 to FIG. 4. The optical module 1 is an E/O module that converts an electric signal into an optical signal and transmits the optical signal.

Note that all the drawings are schematic and relations between thicknesses and widths of respective portions, ratios of thicknesses of the respective portions, and the like are different from real ones. Portions, relations and ratios of dimensions of which are different from one another, are sometimes included among the drawings. Illustration of a part of components, for example, a resin member 45 is sometimes omitted.

The optical module 1 includes an optical element 30, a first wiring board 10, a ferrule 40, which is a holding member, an optical fiber 50, side surface wiring boards 20A and 20B, and signal cables 60.

Note that one character at the end of a sign is sometimes omitted when each of a plurality of components having the same configuration is referred to. For example, each of the side surface wiring boards 20A and 20B is referred to as side surface wiring board 20.

The optical element 30 is a vertical cavity surface emitting laser (VCSEL) including a light emitting section 31 that outputs an optical signal along an optical axis O perpendicular to a front surface 30SA. The optical element 30 is an ultra-small type, a size of a cross section in an optical axis orthogonal direction, that is, a plan view dimension of which is 250 μm×250 μm. The optical element 30 includes, on the front surface 30SA, the light emitting section 31 having a diameter of 10 μm and two external terminals 32 having a diameter of 70 μm connected to the light emitting section 31.

The first wiring board 10 includes a first principal plane 10SA and a second principal plane 10SB opposite to the first principal plane 10SA. The optical element 30 is mounted on the first principal plane 10SA. In other words, although not shown in the figures, the external terminal 32 of the optical element 30 is bonded to a bonding electrode on the first principal plane 10SA. The bonding electrode is connected to an electrode 21 and the like of the side surface wiring board 20 via a wire.

The side surface wiring boards 20A and 20B have substantially the same configuration. The side surface wiring board 20 includes a third principal plane (an inner surface) 20SA and a fourth principal plane (an outer surface) 20SB opposite to the third principal plane 20SA. The third principal plane 20SA and the fourth principal plane 20SB are disposed in parallel to the optical axis O (a Z axis). An end face 20SS of the side surface wiring board 20 is connected to an outer peripheral portion of the second principal plane 10SB of the first wiring board 10.

Note that, in this embodiment, the first wiring board 10 and the side surface wiring boards 20A and 20B are an integral three-dimensional wiring board 19 made of ceramic and include not-shown wires.

The front surface 30SA of the optical element 30 is parallel to the first principal plane 10SA (an XY plane) of the first wiring board 10. In other words, the optical axis O is parallel to the Z axis perpendicular to the first principal plane 10SA. Note that the first wiring board 10 does not have high light transmittance. Therefore, a through hole H10 functioning as an optical path is formed in the first wiring board 10.

The two side surface wiring boards 20A and 20B are disposed to be opposite to each other across the optical axis O (the ferrule 40).

The electrodes 21 are respectively disposed on the fourth principal planes 20SB of the side surface wiring boards 20A and 20B. The number of electrodes 21 is the same as the number of signal cables 60.

For example, the signal cables 60 transmit electric signals to the optical element 30. Lead wires at distal end portions of the signal cables 60 are bonded to the electrodes 21 of the side surface wiring boards 20A and 20B via not-shown solder. In other words, the electrodes 21 and the distal end portions of the signal cables 60 are disposed in parallel to the optical axis O (the Z axis).

For example, the optical fiber 50 includes a core having a diameter of 50 μm that transmits an optical signal and a clad having a diameter of 125 μm that covers an outer circumference of the core.

The ferrule 40 is a rectangular parallelepiped, a sectional shape of which in the optical axis orthogonal direction is a rectangle. The ferrule 40 includes four side surfaces 40SS. In the ferrule 40 is a through hole H40 piercing through an upper surface and a lower surface. A distal end portion of the optical fiber 50 is inserted into the through hole H40.

Positioning of the light emitting section 31 of the optical element 30 and the optical fiber 50 is performed by inserting and fitting the optical fiber 50 into the through hole H40. In other words, the ferrule 40 is disposed on the second principal plane 10SB of the first wiring board 10 in a state in which a center axis of the through hole H40 is disposed to coincide with an optical axis of the optical element 30. An inner shape of the through hole H40 may be, besides a columnar shape, a prism shape such as a quadrangular prism shape or a hexagonal prism shape as long as the optical fiber 50 can be held by the wall surface of the through hole H40.

The material of the ferrule 40 is a metal member such as SUS, ceramic, silicon, or glass. As explained below, the ferrule 40 may be a substantial column, cone, or prism.

The resin member 45 is filled in a space that is surrounded by the side surface wiring boards 20A and 20B and in which the ferrule 40 is disposed. The resin member 45 is made of, for example, epoxy resin. Note that the resin member 45 is not an essential component of the optical module. However, the optical module 1 in which the ferrule 40 is firmly fixed by the resin member 45 has high reliability.

Figure 3:
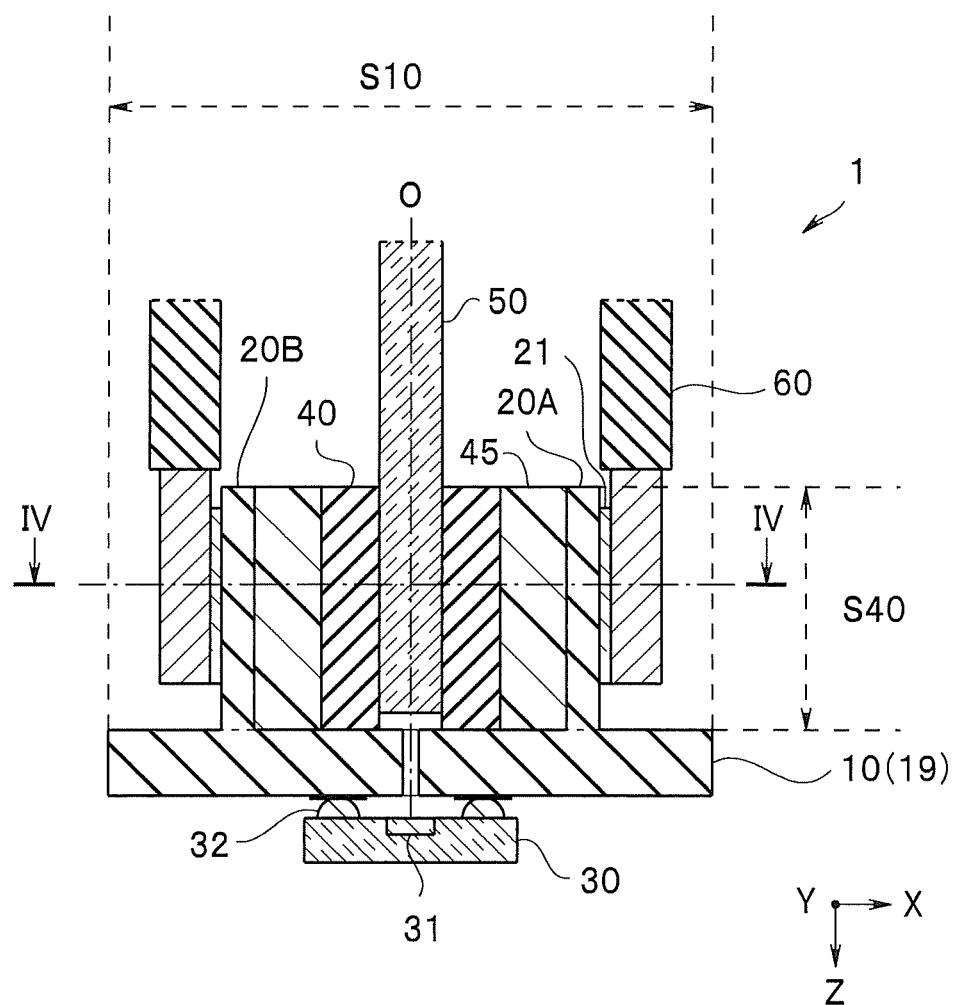
FIG. 3 is a sectional view taken along line III-III of FIG. 2 of the optical module in the first embodiment.
Figure 4:
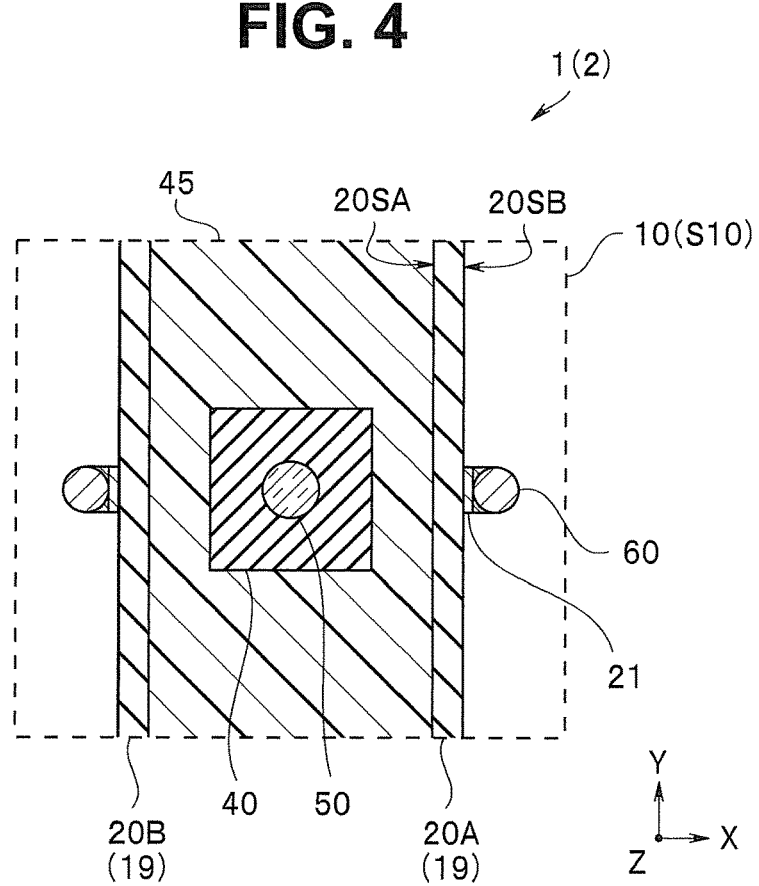
FIG. 4 is a sectional view taken along line IV-IV of FIG. 3 of the optical module in the first embodiment.

Note that, as shown in FIG. 3 and FIG. 4, the optical element 30, the ferrule 40, the side surface wiring boards 20A and 20B, and the distal end portions of the signal cables 60 are included in a first space S10 extending from the first wiring board 10 in the direction of the optical axis O. Therefore, the optical module 1 has a small size in the optical axis orthogonal direction and a narrow diameter.

Further, as shown in FIG. 3, the optical module 1 includes the electrodes 21 of the side surface wiring boards 20A and 20B in a second space S40 extending from the ferrule 40 in a direction orthogonal to the optical axis O.

The ferrule 40 plays a role of a guide for holding the optical fiber 50 perpendicularly to the optical element 30. Therefore, the ferrule 40 needs to have a certain degree of length (height), for example, 0.4 mm to 1.0 mm Length of the bonded sections of the signal cables 60 to the electrodes 21 necessary for securing bonding reliability of the bonded sections is 0.3 mm to 0.4 mm In other words, the bonded sections of the signal cables 60 are included in the space S40. Therefore, the optical module 1 is short and small.

Note that, in the optical module 1, the optical element is a light emitting element including a light emitting section. However, it goes without saying that an optical module in which an optical element is a light receiving element including a light receiving section such as a photodiode has the same effects as the effects of the optical module 1.

<Modifications of the First Embodiment>

Optical modules in modifications of the first embodiment are similar to the optical module 1 and have the same effects as the effects of the optical module 1. Therefore, components having the same functions are denoted by the same reference numerals and sign, and explanation of the components is omitted.

<Modification 1 of the First Embodiment>

Figure 5:
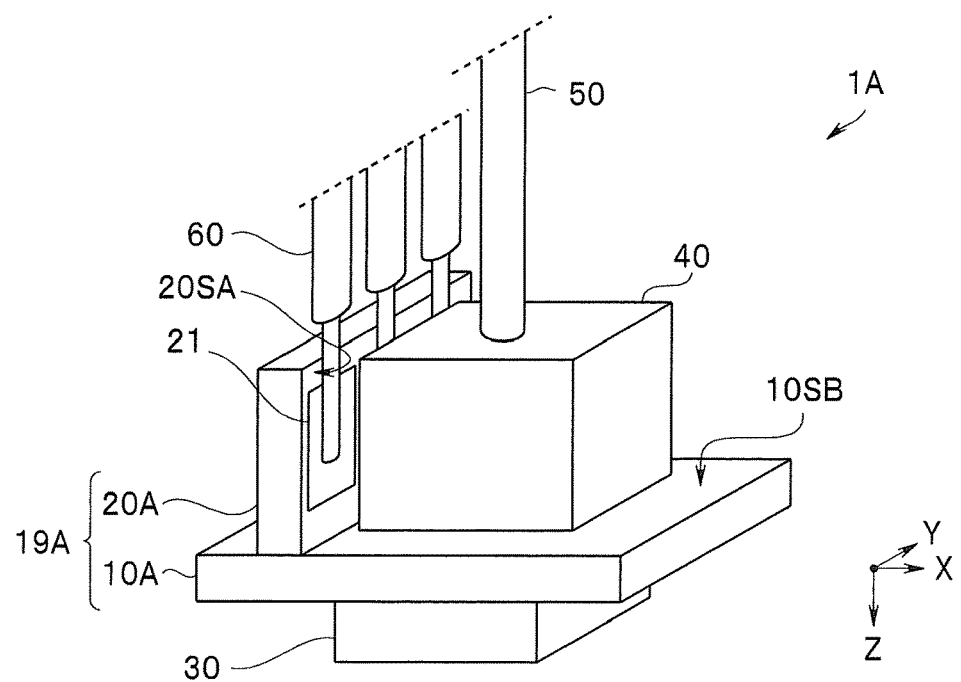
FIG. 5 is a perspective view of an optical module in a modification 1 of the first embodiment.

As shown in FIG. 5, an optical module 1A in a modification 1 of the first embodiment includes one side surface wiring board 20A. An end face of the side surface wiring board 20A is perpendicularly connected to the second principal plane 10SB of the first wiring board 10.

In the optical module 1A, the first wiring board 10 and the side surface wiring board 20A are not an integral three-dimensional wiring board. The first wiring board 10 and the side surface wiring board 20A are respectively rigid wiring boards such as FPC wiring boards, ceramic wiring boards, glass epoxy wiring boards, glass wiring boards, or silicon wiring boards.

The end face of the side surface wiring board 20A is fixed to the second principal plane 10SB of the first wiring board 10 by an adhesive or the like. The wire of the first wiring board 10 and the wire of the side surface wiring board 20A conduct via, for example, conductive paste.

<Modification 2 of the First Embodiment>

Figure 6:
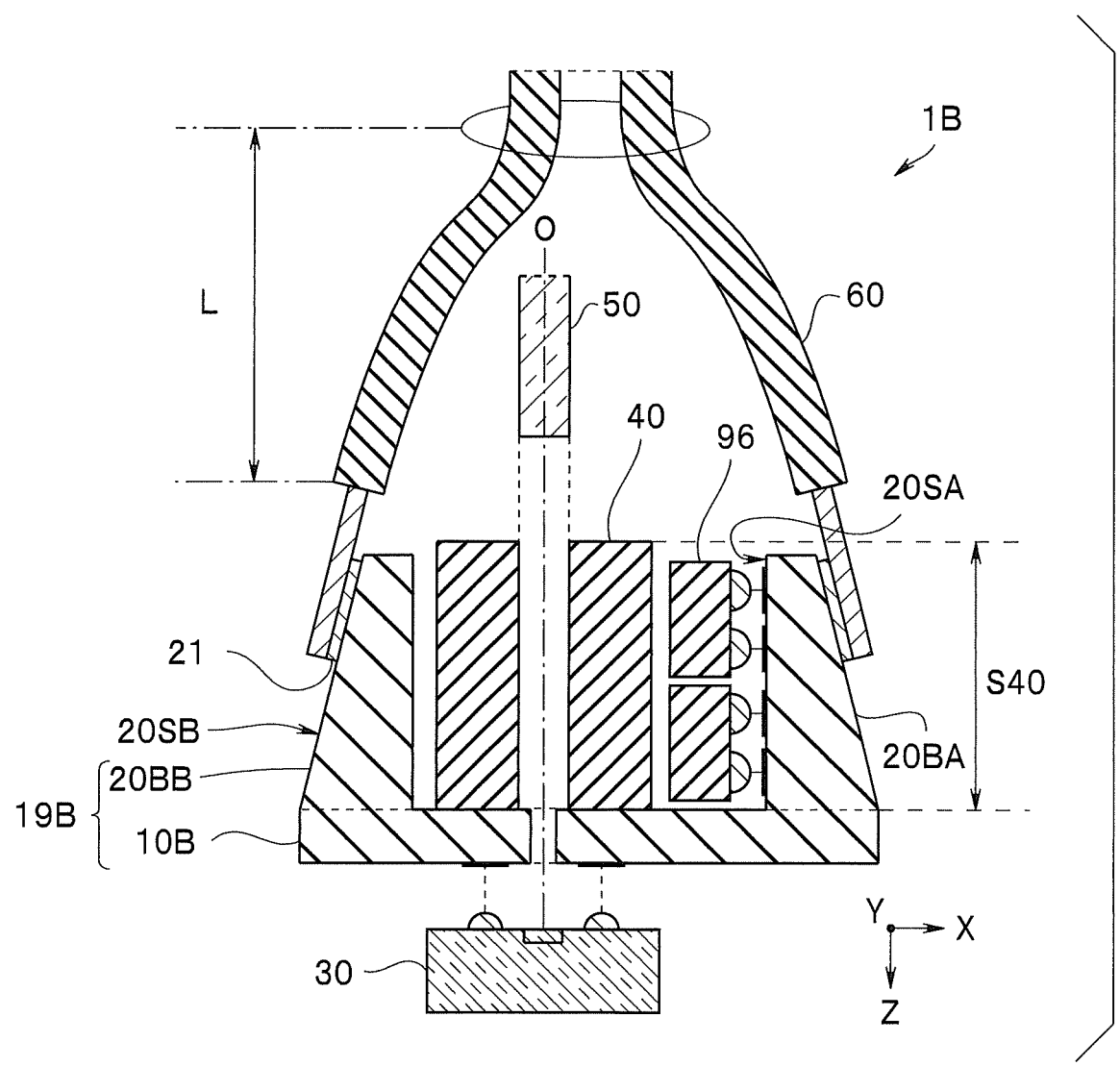
FIG. 6 is a sectional view of an optical module in a modification 2 of the first embodiment.

As shown in FIG. 6, in an optical module 1B in a modification 2 of the first embodiment, a first wiring board 10B and side surface wiring boards 20BA and 20BB are an integral three-dimensional wiring board 19B configured by a molded circuit component (MID: molded interconnect device) having nonconductive resin as a base material and including wires (not shown) and the electrodes 21.

Further, fourth principal planes (outer surfaces) 20SB of the side surface wiring boards 20BA and 20BB on which the electrodes 21 are disposed are inclined with respect to the optical axis O. In other words, an external dimension of a cross section in the optical axis orthogonal direction of the three-dimensional wiring board 19B decreases toward a rear.

A plurality of signal cables 60 are bound in the rear. However, since it is not easy to greatly bend the signal cables 60, length L (a Z-direction dimension) from a bonded section to a bound section of an optical module is sometimes long.

On the other hand, in the optical module 1B in which the electrodes 21 are disposed to incline with respect to the optical axis O, the signal cables 60 approach the optical axis O from the distal end portions toward the rear. Therefore, the length L to the bound section of the optical module 1B is short. The optical module 1B is short and small.

Further, in the optical module 1B, an electronic component 96, which is a chip-shaped surface mounted device (SMD) such as a capacitor, an inductor, or a signal processing IC, is mounted on the third principal plane 20SA of the side surface wiring board 20BA. The electronic component 96 is included in the second space S40 extending from the ferrule 40 in the direction orthogonal to the optical axis O.

In other words, there is a gap between the side surface wiring board 20 and the ferrule 40 in the optical module 1B, since the first wiring board 10B is large. The electronic component 96 is disposed in the gap.

A wire between the optical element 30 and the electronic component 96 is short in the optical module 1B, since the electronic component 96 is mounted in a place near the optical element 30. Therefore, for example, the optical module 1B is less easily affected by noise.

<Modification 3 of the First Embodiment>

Figure 7:
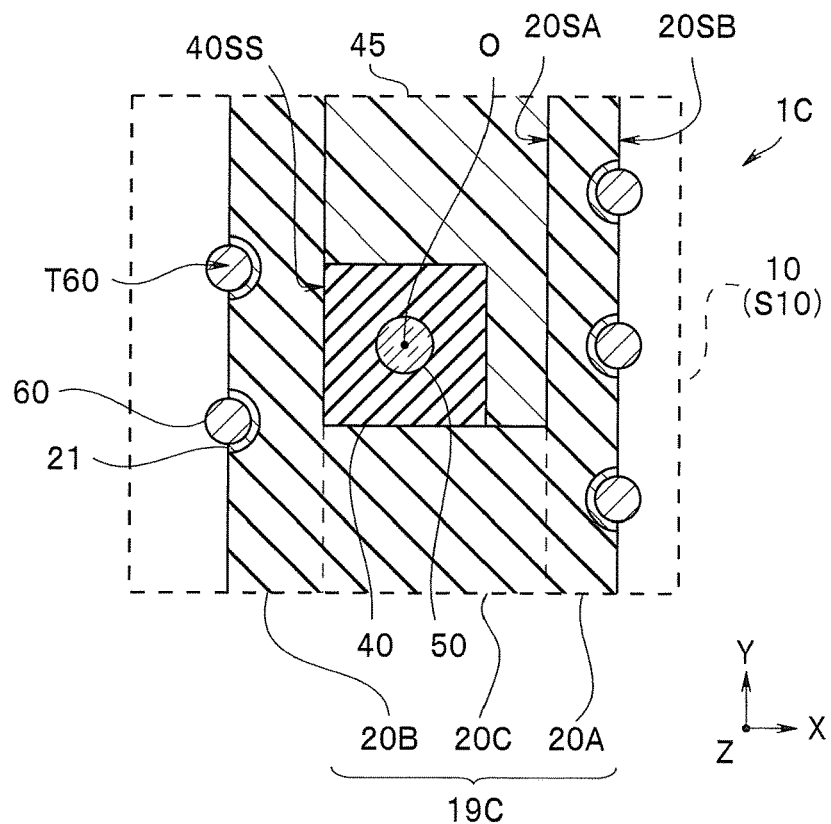
FIG. 7 is a sectional view of an optical module in a modification 3 of the first embodiment.

As shown in FIG. 7, an optical module 1C in a modification 3 of the first embodiment includes side surface wiring boards 20A, 20B, and 20C. The side surface wiring boards 20A and 20B are disposed to be opposite to each other. The side surface wiring board 20C is disposed orthogonally to the side surface wiring boards 20A and 20B.

The side surface wiring boards 20A, 20B, and 20C are a part of a three-dimensional wiring board 19C made of ceramic. Therefore, the side surface wiring boards 20A, 20B, and 20C are not clearly divided.

Two surfaces among the four outer peripheral surfaces 40SS of the ferrule 40 are in contact with the third principal planes 20SA of the side surface wiring boards 20B and 20C disposed orthogonally to each other.

The two outer peripheral surfaces 40SS of the ferrule 40 are respectively in contact with the third principal planes 20SA of the side surface wiring boards 20B and 20C. Consequently, positioning in an in-plane direction (an XY direction) of the optical axis O of the optical element 30 and the center axis of the through hole H40, that is, the optical axis O of the optical fiber 50 is performed.

Note that positioning in an in-plane one direction (an X direction or a Y direction) can be performed even if the ferrule 40 is in contact with only one surface of the side surface wiring board 20. The ferrule 40 may be in contact with three surfaces or four surfaces of the side surface wiring board 20. However, in this case, for example, accurate machining accuracy of an external dimension of the ferrule 40 is required. Therefore, the ferrule 40 is desirably in contact with only the orthogonal two surfaces of the side surface wiring board 20.

Note that the first wiring board 10 and the side surface wiring board 20 are desirably the integral three-dimensional wiring board 19 when the positioning of the ferrule 40 is performed using the side surface wiring board 20. This is because relative positions of the through hole H10 functioning as the optical path of the first wiring board 10 and the side surface wiring board 20 are determined during manufacturing of the three-dimensional wiring board 19.

Further, in an optical module 1C, grooves T60 having a semicircular shape in section according to a shape of the distal end portions of the signal cables 60 are present on the fourth principal planes 20SB. The electrodes 21 are disposed on inner surfaces of grooves T60.

Therefore, in the optical module 1C, bonding reliability of the signal cables 60 and the electrodes 21 is high.

Note that the optical module 1C includes a large number of signal cables 60. In other words, the optical module 1C transmits, with the signal cables 60, electric signals to not-shown other members other than the optical element 30.

<Modification 4 of the First Embodiment>

Figure 8:
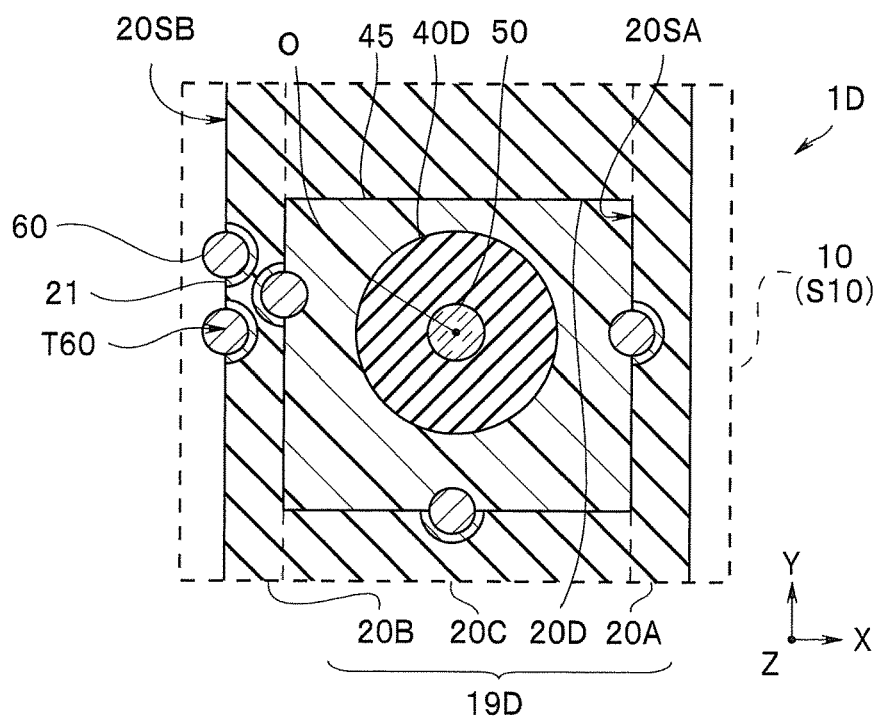
FIG. 8 is a sectional view of an optical module in a modification 4 of the first embodiment.

As shown in FIG. 8, an optical module 1D in a modification 4 of the first embodiment includes four side surface wiring boards 20A, 20B, 20C, and 20D. The side surface wiring boards 20A, 20B, 20C, and 20D disposed to surround a ferrule 40D are a part of a three-dimensional wiring board 19D.

The ferrule 40D is surrounded by the side surface wiring boards 20A, 20B, 20C, and 20D concatenated without a gap.

The signal cables 60 are bonded to the electrodes 21 on the third principal plane 20SA and the fourth principal plane 20SB of the side surface wiring board 20. Note that the electrode 21 may be disposed only on the third principal plane 20SA.

The ferrule 40D has a circular shape as a sectional shape in the optical axis orthogonal direction.

In other words, the number of side surface wiring boards 20 of the optical module of the present invention is one or more and four or less. A plurality of side surface wiring boards 20 only have to be disposed in orthogonal positions or opposite positions if the plurality of side surface wiring boards 20 are disposed to surround the ferrule 40. For example, when the optical module includes three side surface wiring boards 20, two side surface wiring boards are disposed in opposite positions and one side surface wiring board is disposed in a position orthogonal to the other two side surface wiring boards. Note that distances from the optical axis O to the respective side surface wiring boards 20 may not be the same. The plurality of side surface wiring boards 20 may have different shapes (widths/thicknesses).

In the side surface wiring board 20, the electrode 21 is disposed on at least one of the third principal plane 20SA and the fourth principal plane 20SB. When the optical module includes a plurality of side surface wiring boards, the electrode 21 only has to be disposed on at least any one of the plurality of side surface wiring boards.

<Modification 5 of the First Embodiment>

Figure 9:
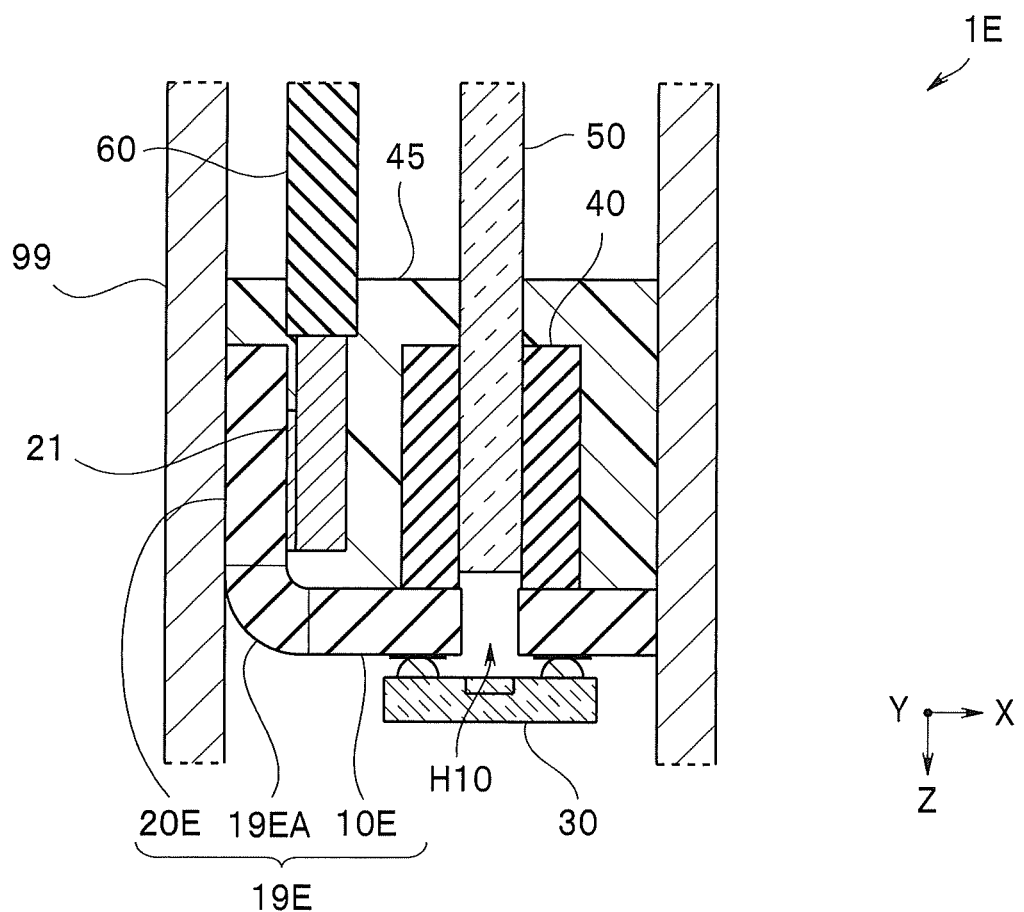
FIG. 9 is a sectional view of an optical module in a modification 5 of the first embodiment.

As shown in FIG. 9, in an optical module 1E in a modification 5 of the first embodiment, a first wiring board 10E and a side surface wiring board 20E are an integral wiring board 19E, a connecting section 19EA of which is flexible. The first wiring board 10E and the side surface wiring board 20E are rigid wiring boards.

Note that the entire wiring board 19E may be flexible. For example, when a flexible base body of the wiring board 19E has high light transmittance like polyimide, the through hole H10 functioning as the optical path of an optical signal is unnecessary. In other words, the through hole H10 of the first wiring board 10 is not an essential component.

In the optical module 1E, the wiring board 19E and the like are disposed on an inside of a tubular member 99. The resin 45 is filled in a space on the inside of the tubular member 99.

In the optical module 1E, the optical element 30, the signal cable 60, and the ferrule 40 can be disposed on the flat wiring board 19E. After a constituent member is disposed, the wiring board 19E is formed three-dimensionally by bending the connecting section 19EA. The wiring board 19E is disposed on the inside of the tubular member 99. Therefore, the optical module 1E is easily manufactured.

Note that the tubular member 99 may be a member common to other members rather than being an exterior member of the optical module 1D. For example, the wiring board 19E and the like may be inserted into a through hole formed at a distal end hard portion of an endoscope and fixed by the resin 45.

<Second Embodiment>

Figure 10:
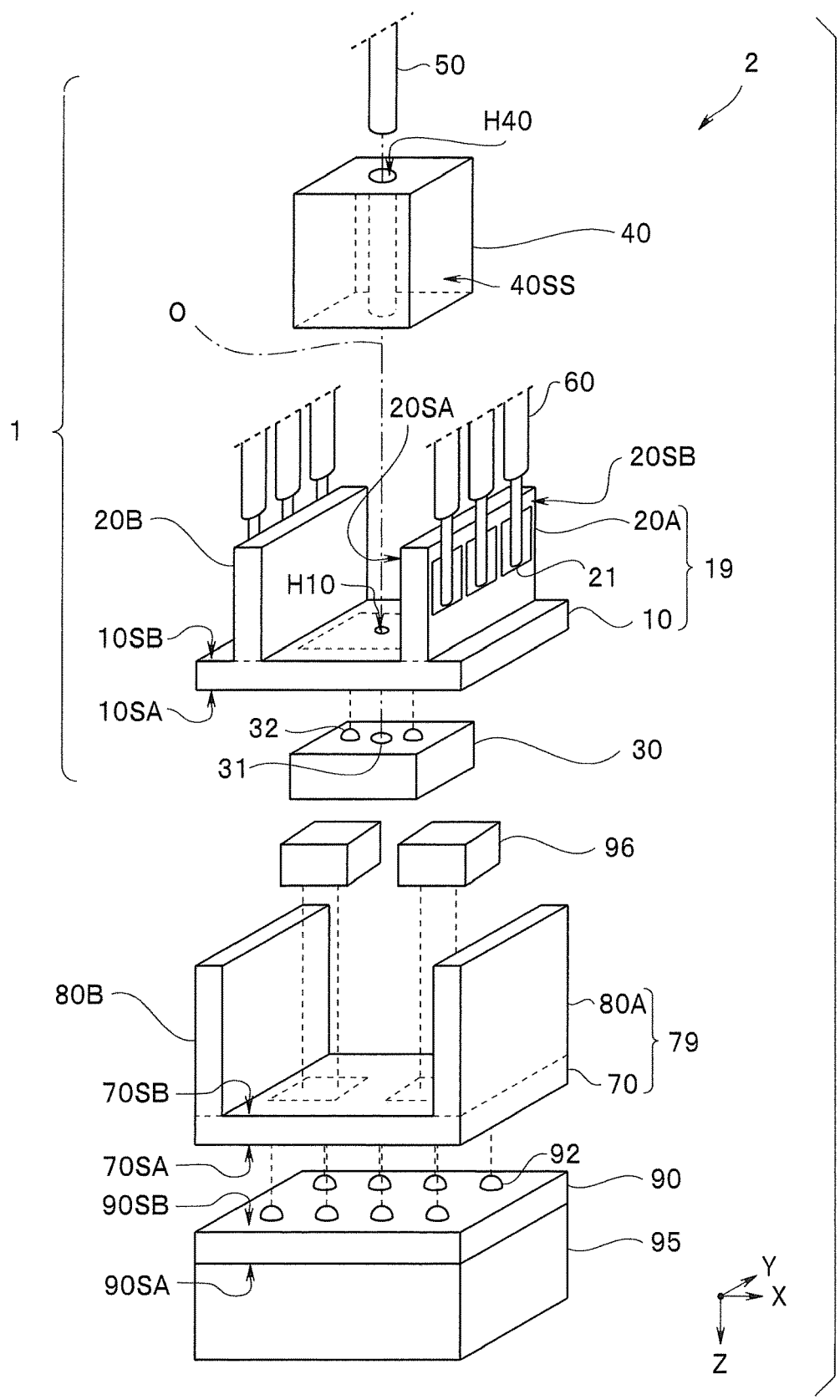
FIG. 10 is an exploded view of an image pickup module in a second embodiment.
Figure 11:
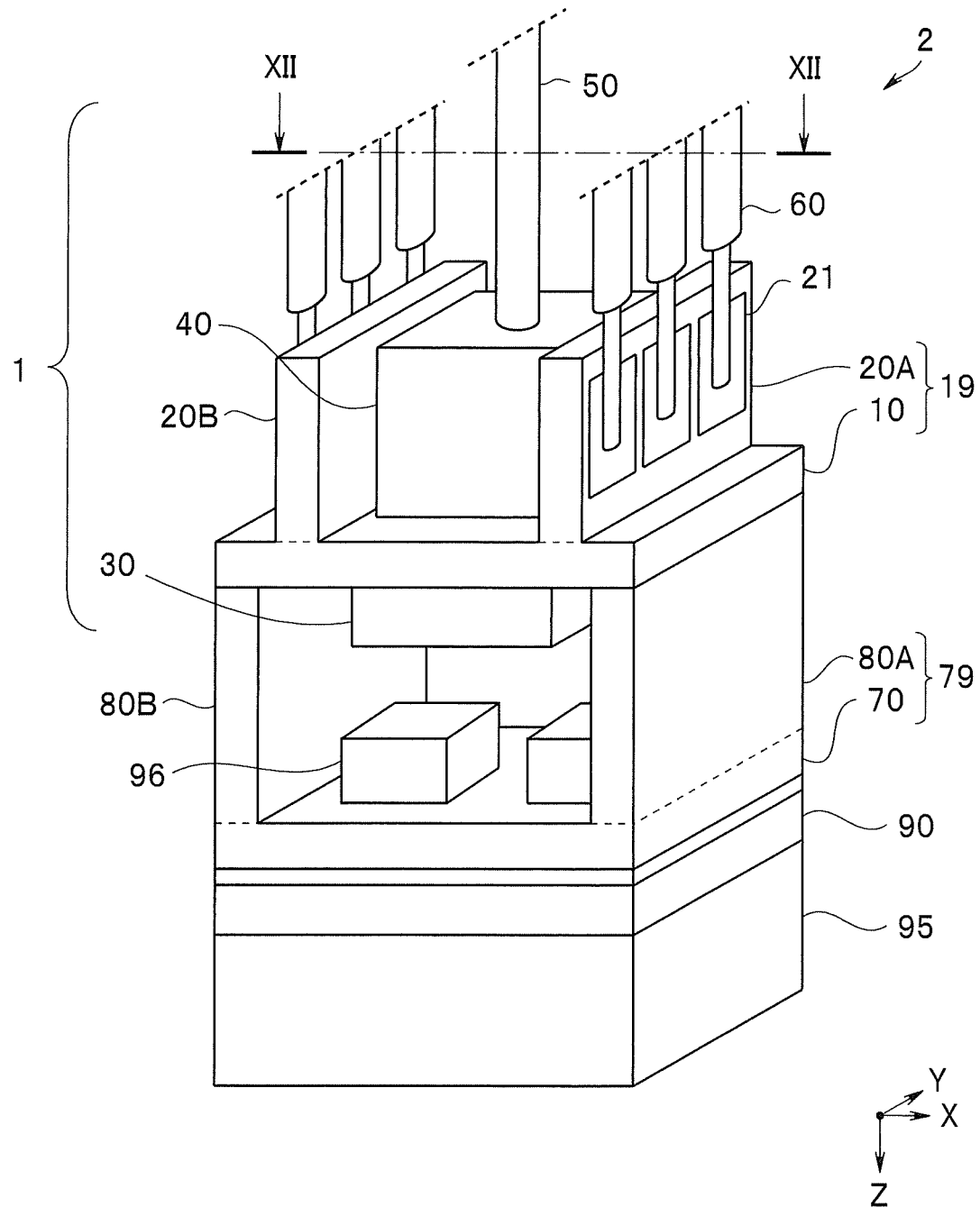
FIG. 11 is a perspective view of the image pickup module in the second embodiment.
Figure 12:
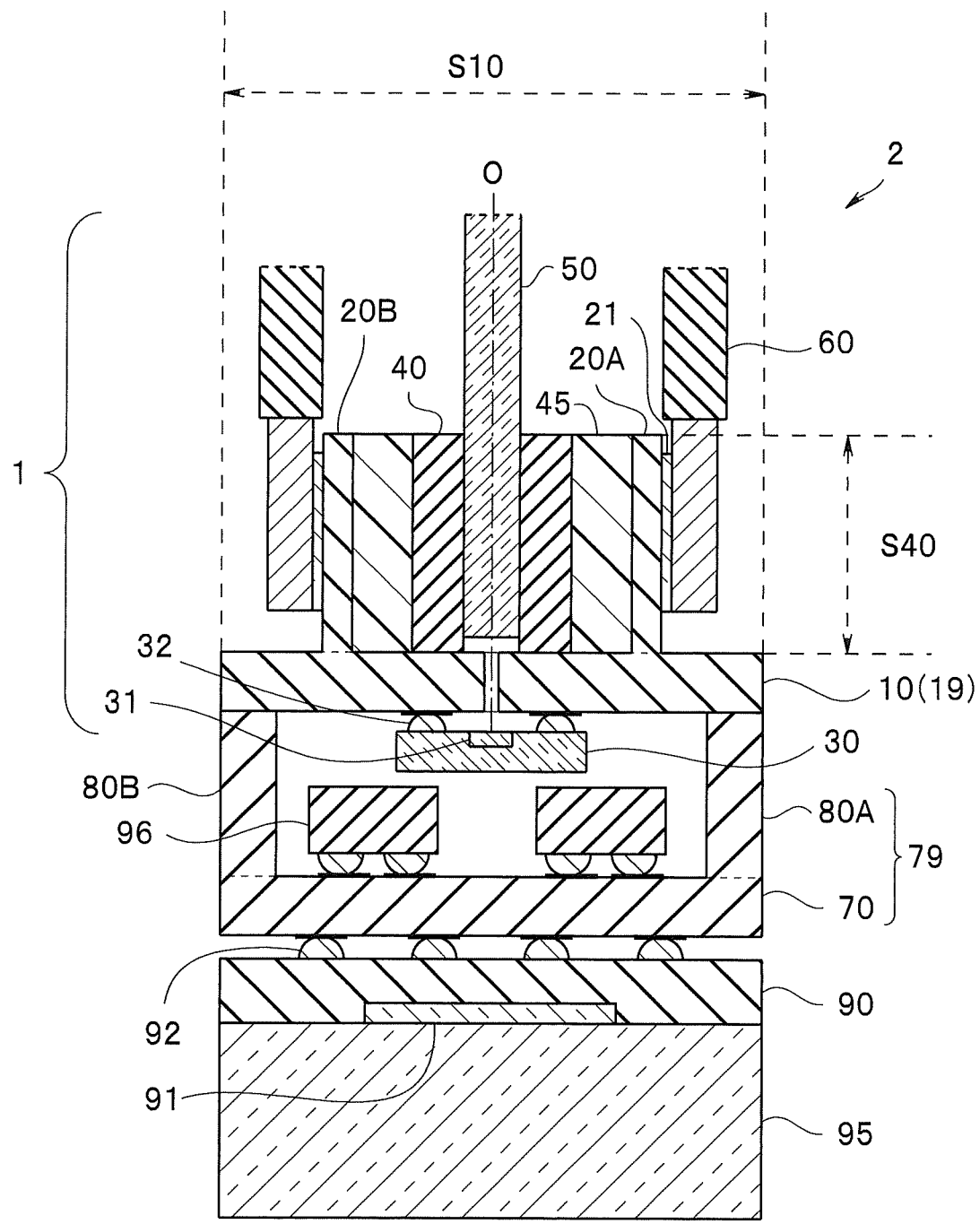
FIG. 12 is a sectional view taken along line XII-XII of FIG. 11 of the image pickup module in the second embodiment.

As shown in FIG. 10 to FIG. 12, an image pickup module 2 in this embodiment includes the optical module 1 in the first embodiment, an image pickup device 90, a second wiring board 70, and interconnecting wiring boards 80A and 80B.

The signal cables 60 transmit electric signals to the image pickup device 90 and the like. An image pickup signal outputted by the image pickup device 90 is converted into an optical signal by the optical element 30 and transmitted via the optical fiber 50.

The image pickup device 90 includes a light receiving surface 90SA and a rear surface 90SB opposite to the light receiving surface 90SA and is configured to output an image pickup signal. A light receiving section 91 such as a CCD or CMOS light reception circuit is formed on the light receiving surface 90SA of the image pickup device 90. The light receiving section 91 is connected to a bonding terminal 92 of the rear surface 90SB via a through wire (not shown) by a through-silicon via (TSV). A cover glass 95 for protecting the light receiving section 91 is bonded to the light receiving surface 90SA.

The second wiring board 70 includes a fifth principal plane 70SA and a sixth principal plane 70SB opposite to the fifth principal plane 70SA. The image pickup device 90 is bonded to the fifth principal plane 70SA.

The interconnecting wiring boards 80A and 80B connect the first wiring board 10 and the second wiring board 70. In other words, in this embodiment, the image pickup module 2 includes two interconnecting wiring boards 80A and 80B having the same configuration. One end face of the interconnecting wiring board 80 is disposed perpendicularly to the first principal plane 10SA of the first wiring board 10. The other end face of the interconnecting wiring board 80 is disposed perpendicularly to the sixth principal plane 70SB of the second wiring board 70.

Note that, in this embodiment, the second wiring board 70 and the interconnecting wiring boards 80A and 80B are an integral three-dimensional wiring board 79 made of ceramic.

As shown in FIG. 12, the first wiring board 10, the second wiring board 70, the side surface wiring boards 20A and 20B, the interconnecting wiring boards 80A and 80B, the optical element 30, the ferrule 40, and the distal end portions of the signal cables 60 are included in the space S10 extending from the image pickup device 90 in the optical axis O direction. Therefore, the image pickup module 2 has a narrow diameter.

In particular, the image pickup device 90 including a large number of pixels has a large plan view size. Therefore, it is possible to easily dispose the side surface wiring boards 20A and 20B and the signal cables 60 around the ferrule 40.

Note that the optical element 30 is housed in a space formed by the interconnecting wiring boards 80A and 80B. In this embodiment, the chip-shaped electronic component 96 such as a capacitor, an inductor, or a signal processing IC is mounted on the sixth principal plane 70SB of the second wiring board 70 opposite to the rear surface 90SB of the image pickup device 90. The electronic component 96 is housed in the same space as the optical element 30.

A distance between the image pickup device 90 and the electronic component 96 is slightly larger than thickness of the second wiring board 70. The image pickup device 90 and the electronic component 96 are close to each other. If, for example, a decoupling capacitor is disposed in a position close to the image pickup device 90, it is possible to efficiently reduce the influence of noise.

Note that the electronic component 96 may be mounted on the principal plane of any of the first wiring board 10, the second wiring board 70, the side surface wiring boards 20A and 20B, and the interconnecting wiring boards 80A and 80B as long as the electronic component 96 is in the space S10 extending from the image pickup device 90 in the optical axis O direction.

<Modifications of the Second Embodiment>

Image pickup modules 2A, 2B, 2E, and 2F in modifications of the second embodiment are similar to the image pickup module 2 and have the same effects as the effects of the image pickup module 2. Therefore, components having the same functions are denoted by the same reference numerals and signs and explanation of the components is omitted.

<Modification 1 of the Second Embodiment>

Figure 13:
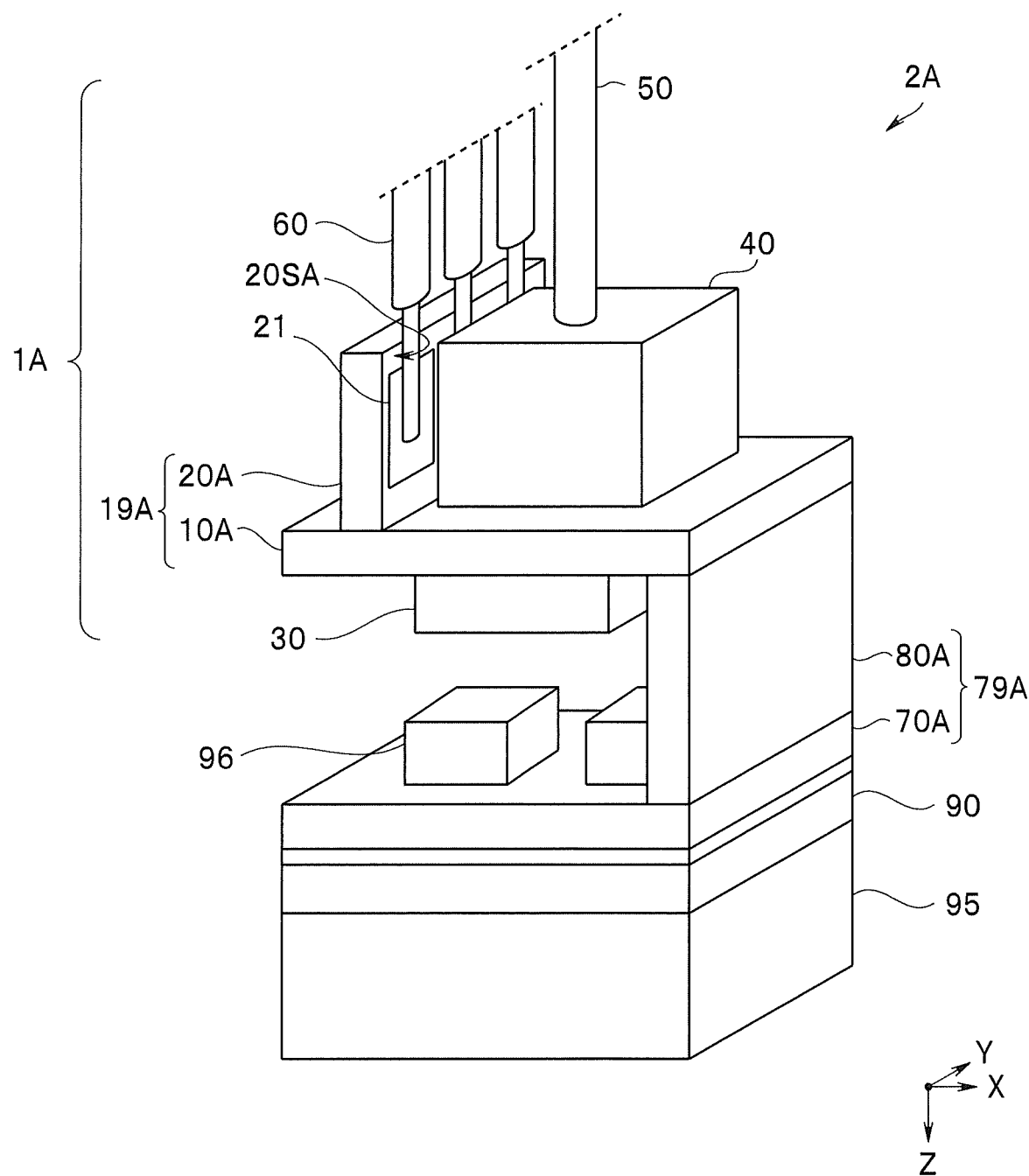
FIG. 13 is a perspective view of an image pickup module in a modification 1 of the second embodiment.

As shown in FIG. 13, the image pickup module 2A in a modification 1 of the second embodiment includes an optical module 1A including one side surface wiring board 20A, the image pickup device 90, a second wiring board 70A, and one interconnecting wiring board 80A.

A principal plane of the interconnecting wiring board 80A that connects a first wiring board 10A and the second wiring board 70 is disposed in parallel to the optical axis O. The principal plane is disposed perpendicularly to the first principal plane 10SA and the sixth principal plane 70SB.

Note that the number of interconnecting wiring boards 80A only has to be one to four like the side surface wiring boards of the optical module 1 explained above. The number of interconnecting wiring boards and the number of side surface wiring boards may be different.

<Modification 2 of the Second Embodiment>

Figure 14:
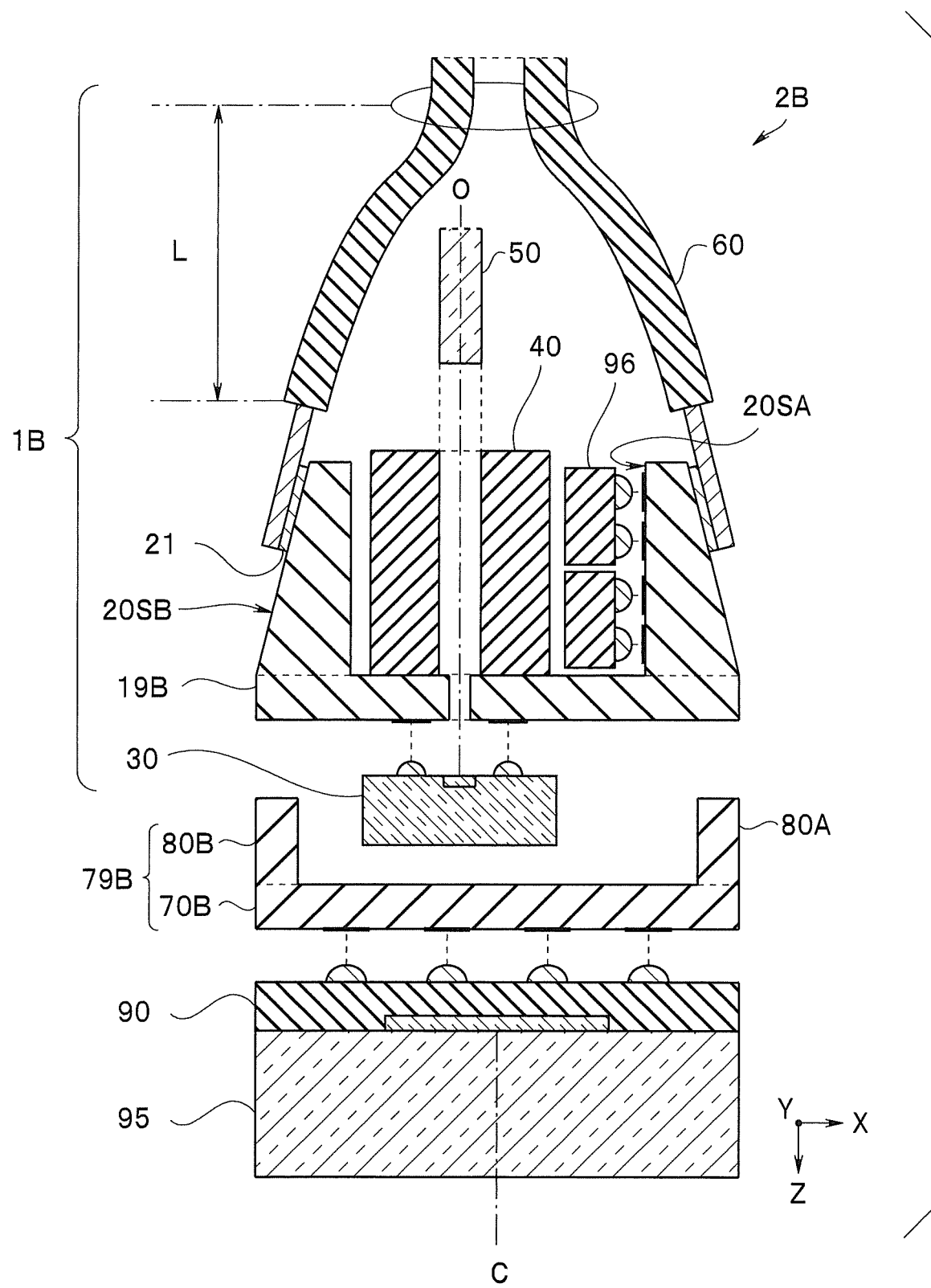
FIG. 14 is a sectional view of an image pickup module in a modification 2 of the second embodiment.

As shown in FIG. 14, the image pickup module 2B in a modification 2 of the second embodiment includes an optical module 1B, the image pickup device 90, and a three-dimensional wiring board 79B including the two interconnecting wiring boards 80A and 80B and a second wiring board 70B.

In the image pickup module 2B, bonding reliability of the signal cables 60 and the electrodes 21 is high. The signal cables 60 can be disposed in positions closer to the optical axis O. Therefore, it is easy to reduce a diameter of the image pickup module 2B.

<Modification 3 of the Second Embodiment>

Figure 15:
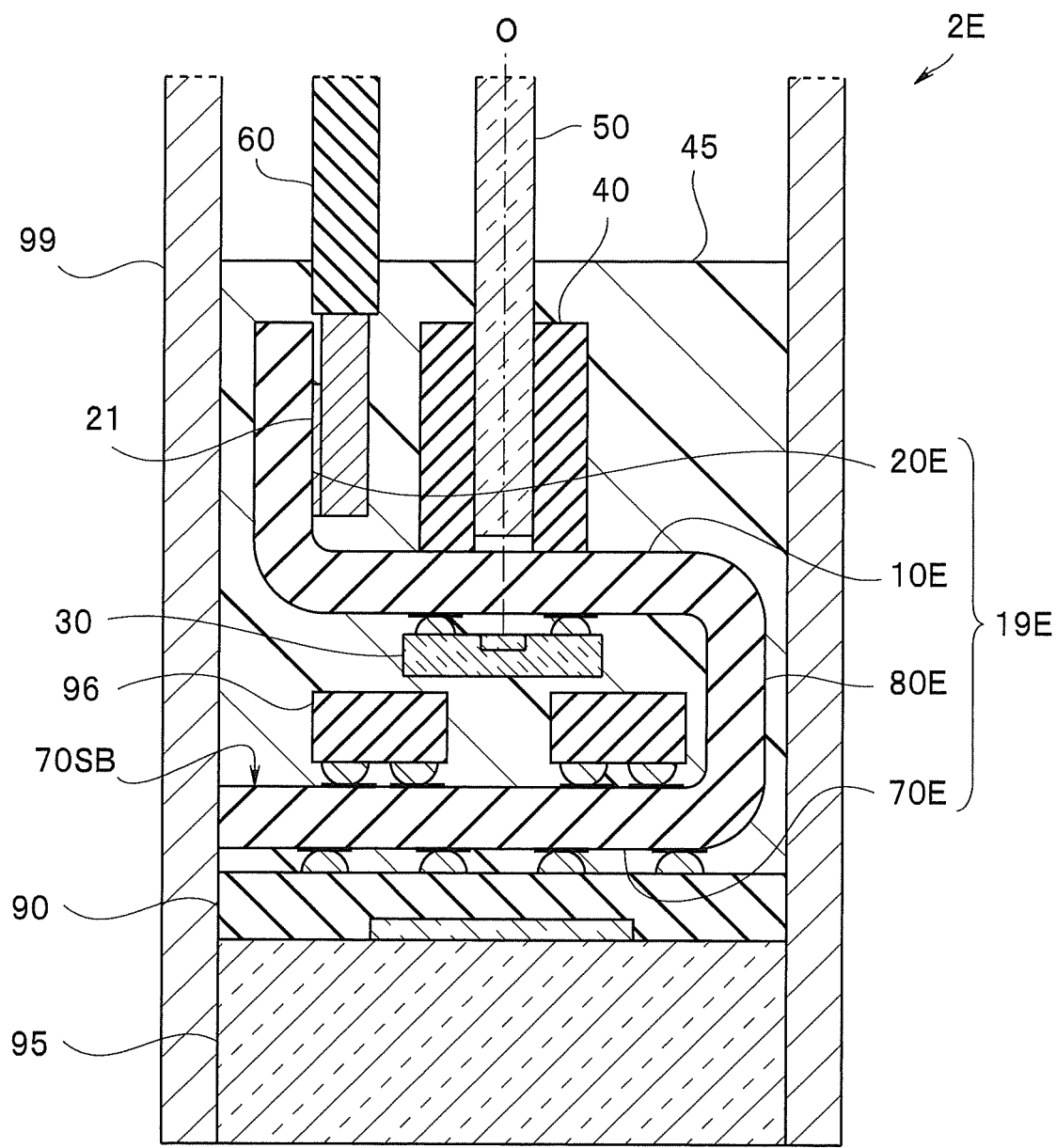
FIG. 15 is a sectional view of an image pickup module in a modification 3 of the second embodiment.

As shown in FIG. 15, the image pickup module 2E in a modification 3 of the second embodiment is similar to the optical module 1E. In the image pickup module 2E, the side surface wiring board 20E, the first wiring board 10E, an interconnecting wiring board 80E, and a second wiring board 70E are a flexible integral three-dimensional wiring board 19E. Note that a through hole functioning as an optical path of an optical signal is not formed in the three-dimensional wiring board 19E, since a base body is made of a light transmissive material such as polyimide.

In the image pickup module 2E, the image pickup device 90 and the like are housed in a hollow section of a housing 99 and sealed by the resin 45. The electronic component 96 is mounted on the sixth principal plane 70SB of the second wiring board 70E.

After the image pickup device 90 and the like are mounted on the wiring board 19E in a flat state, the image pickup module 2E is housed in the housing 99 by bending a connecting section. Therefore, the image pickup module 2E is easily manufactured.

21 Modification 4 of the Second Embodiment>

Figure 16:
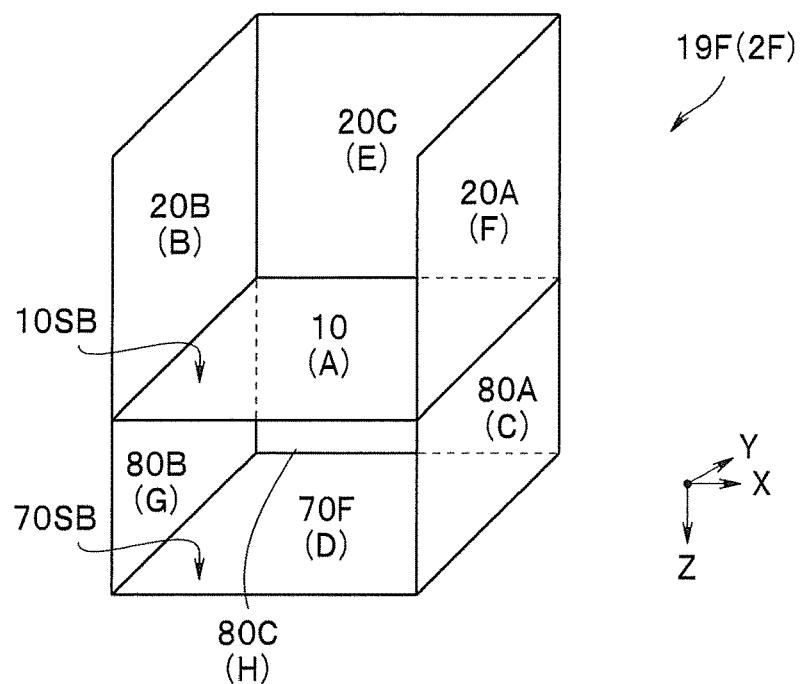
FIG. 16 is a schematic diagram of a wiring board of an image pickup module in a modification 4 of the second embodiment.

As shown in FIG. 16, the image pickup module 2F in a modification 4 of the second embodiment is similar to the image pickup module 2E. The three-dimensional wiring board 19E of the image pickup module 2E includes the one side surface wiring board 20E, the first wiring board 10E, the one interconnecting wiring board 80E, and the second wiring board 70. The image pickup module 2F includes a three-dimensional wiring board 19F including three side surface wiring boards 20A(F), 20B(B), and 20C(E), one wiring board 10(A), three interconnecting wiring boards 80A(C), 80B(G), and 80C(H), and a second wiring board 70F(D), connecting sections of the integral wiring board 19F being flexible.

Figure 17:
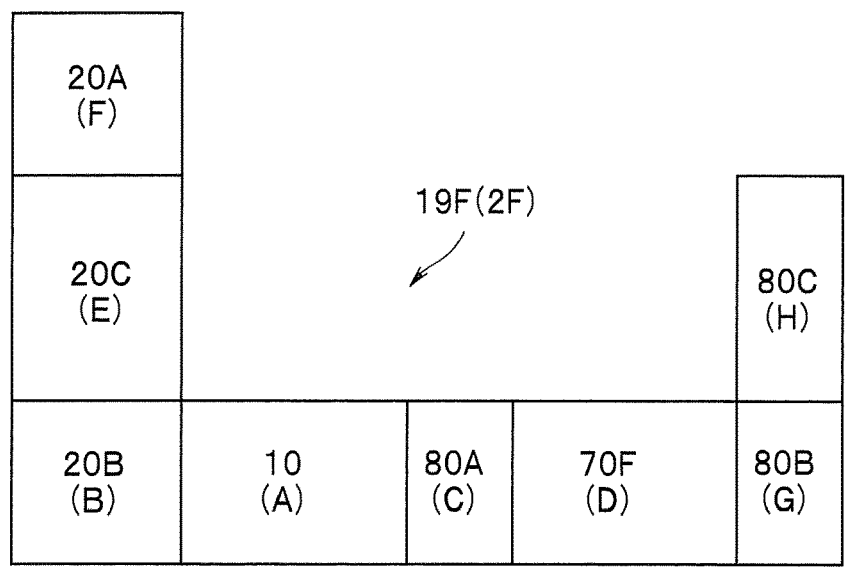
FIG. 17 is a development diagram of the wiring board of the image pickup module in the modification 4 of the second embodiment.

As shown in FIG. 17, in the flat wiring board 19F, for example, the side surface wiring board 20A(F) and the side surface wiring board 20C(E) are connected via a connecting section on a side surface. For example, orthogonal two side surfaces of the side surface wiring board 20B(B) are connected to the side surface wiring board 20C(E) and the first wiring board 10(A) via connecting sections of the two side surfaces.

The flat wiring board 19F is formed as a three-dimensional wiring board 19F by bending a connecting section. Before the bending, an optical element, a signal cable, a ferrule, and the like can be disposed on the wiring board 19F. Therefore, the image pickup module 2F can be easily manufactured.

Note that the entire three-dimensional wiring board 19F may be flexible. The three-dimensional wiring board 19F may include one to four side surface wiring boards and one to four interconnecting wiring boards.

<Third Embodiment>

An endoscope 9 in a third embodiment includes the image pickup module 2 (or 2A, 2B, 2E, or 2F) explained above.

Figure 18:
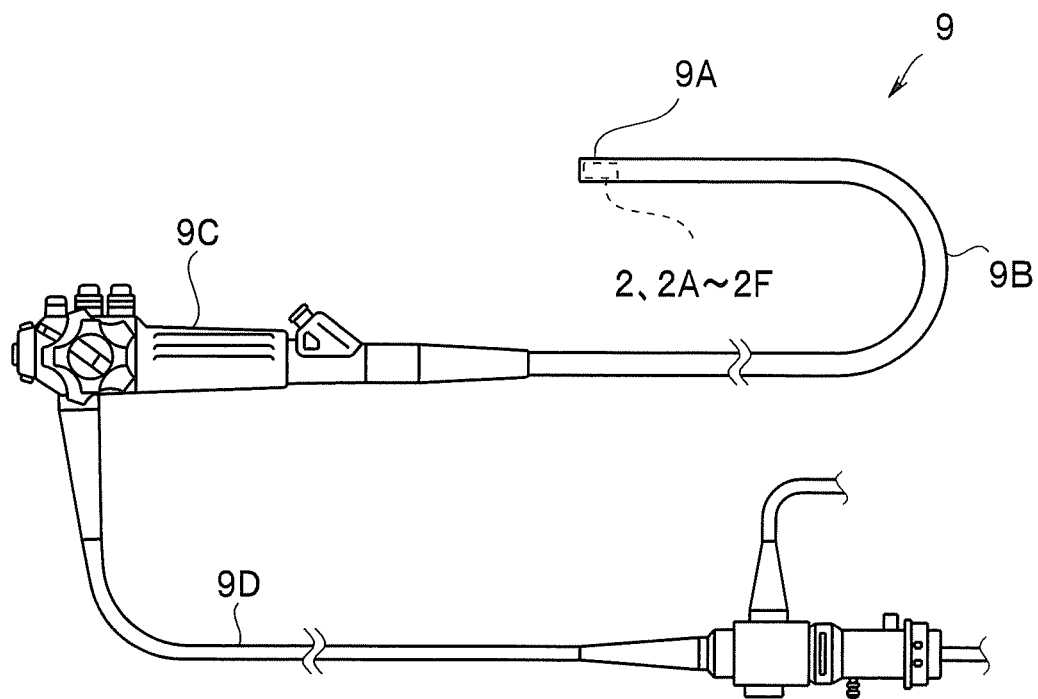
FIG. 18 is a perspective view of an endoscope in a third embodiment.

As shown in FIG. 18, the endoscope 9 includes an insertion section 9B in which the short and small image pickup module 2 with a narrow diameter is housed in a distal end portion 9A, an operation section 9C disposed on a proximal end side of the insertion section 9B, and a universal cord 9D extended from the operation section 9C. The universal cord 9D is connected to the signal cable 60 of the image pickup module.

The endoscope 9 includes, at the distal end portion 9A of the insertion section 9B, the short and small image pickup module 2 with a narrow diameter. Therefore, the endoscope 9 is minimally invasive. Note that the endoscope 9 is a flexible endoscope but may be a rigid endoscope. The endoscope in the embodiment may be a medical endoscope or may be an industrial endoscope.

The present invention is not limited to the embodiments or the modifications explained above. Various changes, combinations, and applications are possible within a range not departing from the gist of the invention.

What is claimed is:

1. An optical module comprising:
   an optical element including a light source or an image sensor;
   a first wiring board including a first principal plane and a second principal plane opposite to the first principal plane, the optical element being mounted on the first principal plane;
   a holding member disposed on the second principal plane of the first wiring board such that a center axis of a through hole coincides with an optical axis of the optical element;
   an optical fiber inserted into the through hole of the holding member;
   a side surface wiring board including a third principal plane and a fourth principal plane opposite to the third principal plane, the third principal plane being disposed in parallel to the optical axis, an end portion of the side surface wiring board being connected to the first wiring board, an electrode being disposed on at least one of the third principal plane and the fourth principal plane; and
   a signal cable having a distal end portion bonded to the electrode of the side surface wiring board, wherein
   the side surface wiring board extends to a second principal plane side of the first wiring board;
   the optical element, the holding member, the side surface wiring board, and the distal end portion of the signal cable are included in a first space extending from the first wiring board in a direction of the optical axis, and
   the electrode of the side surface wiring board is included in a second space extending from the holding member in a direction orthogonal to the optical axis.

2. The optical module according to claim 1, wherein
   the electrode is disposed on the fourth principal plane of the side surface wiring board, and
   the fourth principal plane is disposed in parallel to the optical axis.

3. The optical module according to claim 1, wherein
   the electrode is disposed on the fourth principal plane of the side surface wiring board, and
   the fourth principal plane is inclined with respect to the optical axis.

4. The optical module according to claim 2, wherein a plurality of side surface wiring boards are disposed in orthogonal positions or opposite positions to surround the ferrule.

5. The optical module according to claim 4, wherein the optical module includes a resin member that fills a space in which the holding member is disposed, the space being surrounded by the plurality of side surface wiring boards.

6. The optical module according to claim 1, wherein the first wiring board and the side surface wiring board are an integral three-dimensional wiring board made of ceramic or MID.

7. The optical module according to claim 6, wherein an outer peripheral surface of the holding member and the third principal plane of the side surface wiring board are in contact.

8. The optical module according to claim 1, wherein at least a connecting section of the first wiring board and the side surface wiring board is a flexible integral wiring board.

* * * * *